US006401044B1

(12) United States Patent
Ibanez Rodriguez et al.

(10) Patent No.: US 6,401,044 B1
(45) Date of Patent: Jun. 4, 2002

(54) INSTALLATION FOR THE AUTOMATIC EVALUATION OF THE ROLLING BAND ON WHEELS OF MOVING TRAINS

(75) Inventors: Alberto Ibanez Rodriguez, Arganda del Rey Madrid; Luis Gomez-Ullate Alvear, Madrid; Jose Javier Anaya Velayos, Madrid; Eugenio Villanueva Martínez, Madrid; Monserrat Parrilla Romero, Madrid; Carlos Fritsch Yusta, Madrid; Teresa Sánchez Martín, Madrid; Angel Luis Sanchez Revuelta, Madrid; Jose Antonio Martos Navarro, Madrid; Antonio Lupianez Garcia, Madrid, all of (ES)

(73) Assignees: Patentes Talgo, S.A.; Consejo Superior de Investigaciones Cientificas, both of Madrid (ES)

( * ) Notice: Subject to any disclaimer, the term of this patent is extended or adjusted under 35 U.S.C. 154(b) by 0 days.

(21) Appl. No.: 09/345,395

(22) Filed: Jul. 1, 1999

(30) Foreign Application Priority Data

Aug. 4, 1998 (ES) ................................................ 9801664

(51) Int. Cl.⁷ .......................... G01N 29/04; G01B 17/00
(52) U.S. Cl. .............................. 702/39; 702/34; 73/636; 73/598
(58) Field of Search .............................. 702/34, 35, 39, 702/81, 155, 171, 159; 73/636, 598

(56) References Cited

U.S. PATENT DOCUMENTS

| | | | |
|---|---|---|---|
| 3,812,708 A | 5/1974 | Cowan et al. | 73/598 |
| 3,978,712 A * | 9/1976 | Cowan et al. | 73/67.5 |
| 4,050,292 A | 9/1977 | Bloch | 73/602 |
| 4,798,964 A | 1/1989 | Schmalfuss et al. | 250/560 |
| 4,866,642 A * | 9/1989 | Obrig et al. | 364/562 |
| 5,212,645 A * | 5/1993 | Wildes et al. | 364/463 |
| 5,287,291 A * | 2/1994 | Cuffe et al. | 364/507 |
| 5,636,026 A * | 6/1997 | Mian et al. | 356/376 |
| 5,654,510 A | 8/1997 | Schneider | 73/622 |
| 5,777,891 A * | 7/1998 | Pagano et al. | 364/507 |

FOREIGN PATENT DOCUMENTS

| | | |
|---|---|---|
| EP | 0555169 | 8/1993 |
| EP | 0751371 | 1/1997 |

OTHER PUBLICATIONS

Von Wolfgang Schmidt, Zeitschriff Fur Eisenbahnwesen und Verkehrstechnik, vol. 114, No. 9/10, ZEV+DET–Glas. Ann. 114 (1990) PP. 347–348.

* cited by examiner

Primary Examiner—Marc S. Hoff
Assistant Examiner—Paul Kim
(74) Attorney, Agent, or Firm—Ladas & Parry

(57) ABSTRACT

An installation for the automatic evaluation of the condition of the rolling band on wheels of moving trains. It comprises a rail beam (1) for each railway line (8), a guard-rail to assure wheel guidance, feelers (P1, P2, P3, P4) intended to come into contact with the wheels passing over them, feeler holders fitted on the rail beam, to ensure wheel-feeler contact, ultrasonics equipment (12) to transmit ultrasonic pulses towards the wheels and to generate the corresponding ultrasonic plots, a local processor (13) to control the ultrasonics equipment and to receive the ultrasonic plot signals generated, a computer (14) connected to the local processor to manage the ultrasonics equipment, and an antenna (15) connected to the computer to identify the compositions of train measurements. The invention is useful to detect cracks in the rolling band of railway vehicle wheels.

13 Claims, 4 Drawing Sheets

INSTALLATION FOR THE AUTOMATIC EVALUATION OF THE ROLLING BAND ON WHEELS OF MOVING TRAINS

FIELD OF THE INVENTION

The present invention refers to an installation for the automatic evaluation of the condition of the rolling band on wheels of moving trains, especially for the detection of cracks in said rolling band, in which ultrasonics are used to produce ultrasonic plots of the wheels when these pass over feelers installed on the track.

BACKGROUND OF THE INVENTION

The prior art has already considered the measurement of certain railway vehicle wheel parameters. Hence, in EP-A-0 751 371, an installation and a process are described to measure parameters such as the flange thickness and height of a railway vehicle wheel, wheel diameter and the distance between inside faces of wheels mounted over the same axle, the measurement being made while the railway vehicle travels at its manoeuvre speed. Another example may be found in U.S. Pat. No. 4,866,642, where railway vehicle wheel diameters are calculated from data obtained by simultaneously producing two marker points on the surface of the rolling band and simultaneously detecting these marker points, as well as from data representing the known fixed position of the marker generators and probes. Likewise, in U.S. Pat. No. 4,798,964 a method and an apparatus are described to measure the quality of the rolling band of railway wheels without contact, by illuminating the circumferential surface of the wheel with a light or radiation source directing its radiation at least more or less in a radial direction over the wheel surface so as to form a luminous image of the profile or of the wheel rolling band.

SUMMARY OF THE INVENTION

Starting from the already known prior art, the invention has developed an installation for the automatic evaluation of the condition of the rolling band on wheels of moving trains, intended to be especially used for the detection of cracks in said rolling band, but may also be used to measure other railway vehicle wheel rolling parameters. This installation basically consists of a support structure, made of steel, formed by a rail beam for each railway line, replacing a section of the latter and over which the flange of the train wheels is made to pass, assuring the continuity between the rail beam and the railway line by means of a bolted joint; a guard-rail attached to each rail beam to ensure the guidance of the wheels while moving, being supported with their flange over the rail beam; feelers intended to come into contact with the wheels passing over them; feeler holders fitted on the rail beam, each one of them being provided with two guides and a swinging spring, such that the passage of the wheels over the feelers forces and assures the wheel-feeler contact; ultrasonics equipment to transmit programmable frequency and duration ultrasonic pulses towards the passing wheels and to generate and acquire ultrasonic plots corresponding to the wheels; a local processor to control the ultrasonic equipment and to digitally receive the signals generated by the ultrasonic plots; a computer connected to the local processor and responsible for giving the activation orders of the ultrasonics equipment, collecting, organizing and storing the measurement results and generating the pertinent reports; and an antenna connected to the computer and destined to identify the measured train compositions.

Conveniently, the feeler holders can be activated and deactivated in order to move vertically by means of two guides provided for such a purpose.

Preferably, the installation of the invention will include at least two feelers for each railway line, but it will also be possible to install four of said feelers for each line.

Each one of the mentioned feelers consists of a piezo-electric transducer to generate and receive superficial ultrasonic waves using a dry coupling means and including two inductive proximity detectors to indicate the presence of a wheel over the transducer. Preferably, the superficial waves generated and received by each transducer are of 1 MHz and the dry coupling means used in each transducer is a film of crude rubber.

According to the invention, the ultrasonics equipment is designed for the generation, acquisition and processing of ultrasonic signals in real time to perform non-destructive tests of materials and includes an analogical part and a digital part. Said analogical part comprises analogical treatment modules for the ultrasonic signals to be acquired, including programmable gain amplifiers and prefiltering, detection, logarithmic amplification and channel multiplexing stages, said programmable gain being 80 dB at 20 MHz and said logarithmic amplification being 100 dB.

Said digital part comprises a bus with segmented architecture and a set of dedicated processing modules of high effectiveness, said bus consisting of segments separated by bases over which the processing modules are housed.

According to the invention, the selection of the processor modules and their installation on the segmented architecture bus, permit the flexible definition of acquisition and processing chains of the "pipeline" type, with a high level of parallelism, adapting to the demands of each application, being possible to reach acquisition speeds of up to 80 Msamples/s with a maintained processing rate of 10 Msamples/s. Physical, processing modules exist with digital and mixed technology and each module has a set of programmable parameters and operation modes. Moreover, some fixed modules may modify their own architecture to execute different algorithms, by means of a software reconfiguration of its internal circuits.

According to the invention, the analogical part of the ultrasonics equipment is housed on an analogic base card serving as a support for the analogical amplification-filter modules across a series of slots with analogical channels in each one of them and containing, moreover, a stabilized voltage generation system, to supply the analogic modules, the input channel selection circuitry and an analogical module for envelope detection, these modules being governed by means of the control bus of said card. Said analogical part also includes an additional slot directly joined to the control bus, which permits to add a digital input-output card, which in the present case is for the detection of the wheels.

On the other hand, the digital part of the ultrasonic equipment is housed on a remote digital base card serving as a support for the digital and hybrid architecture processing modules, which are inserted in baseboards joined to the control bus of said card, each baseboard being joined to the following one by means of the segmented signal bus, through which receives the data processed by the previous module, delivering its results to the following module. Moreover, the output of each module is joined to a results memory. Said digital base card also contains the communications subsystem for the reception of orders and transmission of results, as well as a local processor controlling the entire digital base card and responsible for programming the modules, attending the communications and activating the capture and processing of signals.

Both the analogical base card and digital base card are connected to a power supply.

In a preferred embodiment of the invention, the analogical base card incorporates four slots with two analogical channels each one, and the remote digital base card incorporates four baseboards.

Likewise, according to the invention, the ultrasonics equipment includes a series of programmable pulse generators connected to the feelers and to the amplification modules. One of the aforementioned proximity sensor control modules is installed in the digital input-output slot of the analogical base card and a gain control module, an analogical/digital conversion module and a data reduction module are installed on the remote digital base card.

According to a preferred embodiment of the invention, four programmable pulse generators and two amplification modules are provided, which are installed on the analogical base card, each one of which incorporates two linear variable gain amplifiers.

BRIEF DESCRIPTION OF THE DRAWINGS

The previous and other objects of the invention, as well as their characteristics and specific advantages may be more clearly explained by referring to the following detailed description of an embodiment of the invention shown in the attached drawings, in which.

DETAILED DESCRIPTION OF THE INVENTION

The installation of the invention is a dynamic system used with trains moving at a speed of up to 10 Km/h and, for such a reason, it is necessary to have a mechanical structure assuring the passage of the wheels and serving as a support for the feelers to be applied to the periphery of the wheel rolling bands in order to detect their condition, being necessary to assure at all times the feeler-wheel coupling.

Figure 1:
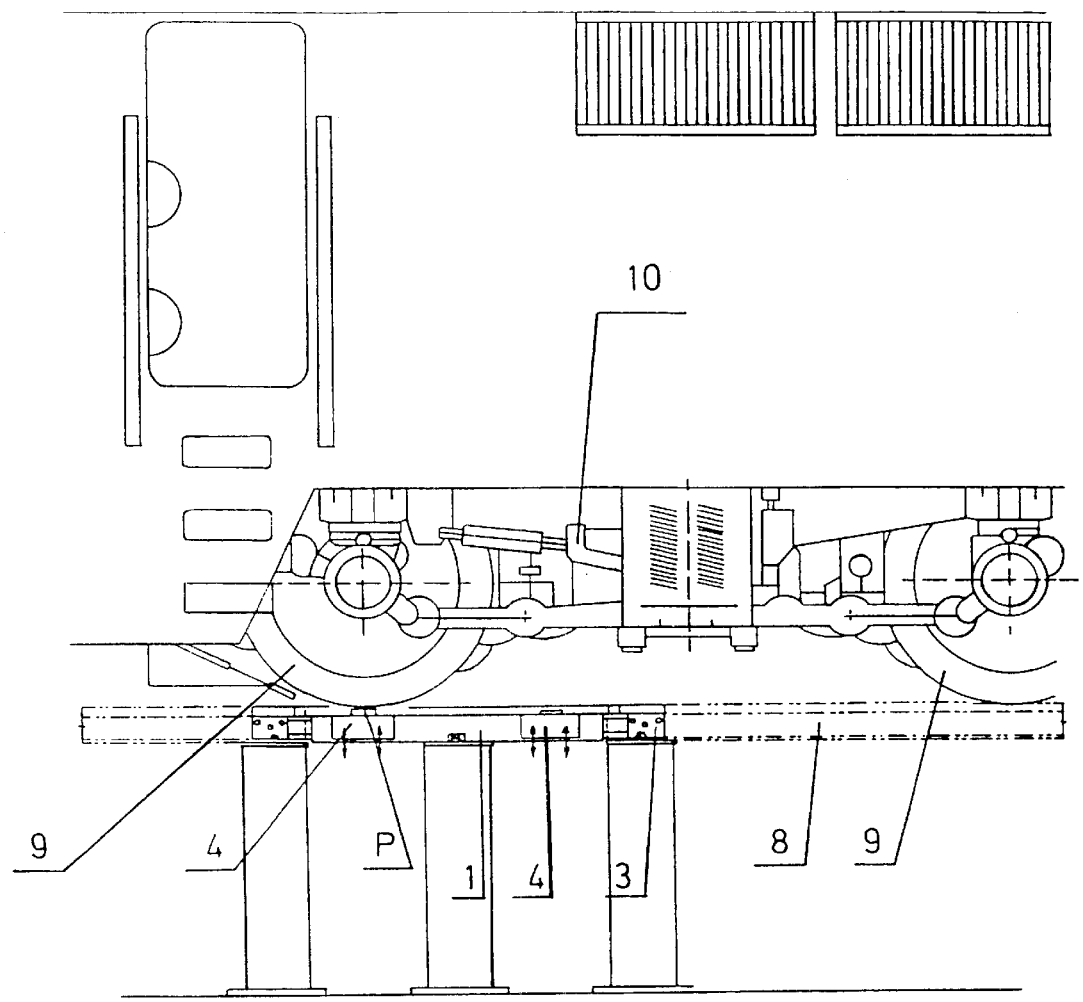
FIG. 1 is a schematic elevation view showing a railway bogie with a wheel located over a feeler of the installation of the invention.
Figure 2:
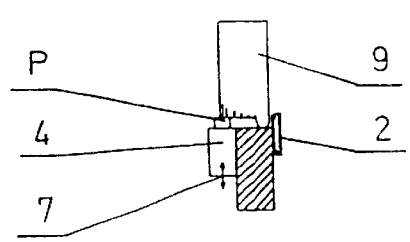
FIG. 2 is a detailed schematic view, showing how a railway wheel is applied to the feeler of the installation of the invention.
Figure 3:
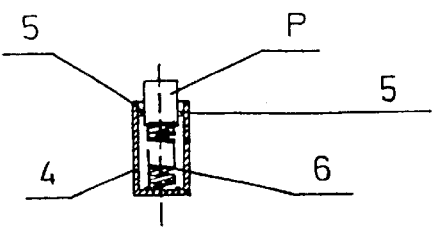
FIG. 3 is a schematic view of a feeler holder of the installation of the invention.

As illustrated in FIGS. 1 to 3, said mechanical support structure is made of steel and comprises a rail beam 1, provided with two guard-rails 2 with the double purpose of assuring the guidance of the wheel 9 at a bogie 10, and acting as a safety measure, given that the wheel passes over the rail beam 1 leaning on its flange. Said rail beam 1, replaces an ordinary railway line section 8, establishing the continuity between the rail beam 1 and the railway line 8, by means of a bolted joint 3.

The rail beam 1 serves as a support for the holders 4 of feeler P intended to be applied to the rolling band of the bogie wheels 9. The holders 4 are each provided with two guides 5 and a swinging spring 6, in such a way that the passage of the wheel 9 forces and assures wheel-feeler contact.

If necessary, each one of said holders 4 may be activated and deactivated to displace them vertically by means of a guide 7.

Each one of the feelers P consists of a piezoelectric transducer to generate and receive surface waves of 1 MHz, said transducers using a crude rubber film as a coupling means. As is shown in FIG. 4, the transducers are installed on a mechanical device assuring the contact thereof with the wheels 9 during their inspection.

Figure 4:
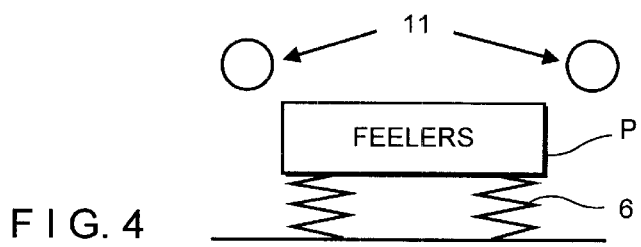
FIG. 4 is a schematic view of a feeler complemented with two inductive detectors.

As is also shown in FIG. 4, each feeler P includes two inductive proximity detectors 11 indicating the presence of a wheel 9 over the transducer.

Figure 5:
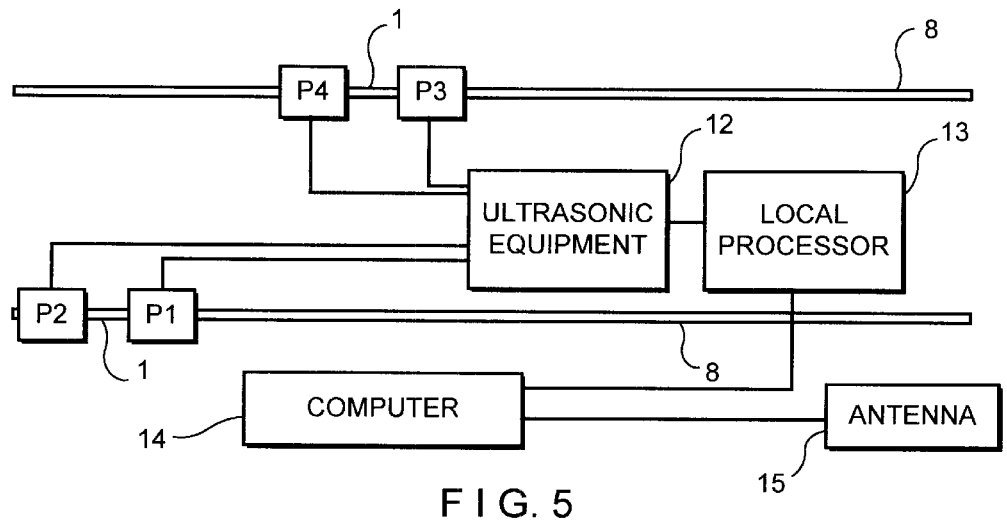
FIG. 5 is a block diagram of the installation of the invention.

The complete installation of the invention is shown in FIG. 5, where four feelers P1, P2, P3 and P4 are shown, which, as has been said, constitute ultrasonic surface wave transmitter-receivers with dry coupling and incorporating wheel presence detectors 11, being provided with mechanical devices 4 to adapt the feeler to the moving wheel 9 and adjust the height over the rail beam 1, as well as the components added to the rail beam 1 (guard-rail 2) to guide the wheel 9. It is possible to instal up to four feelers P for each rail beam 1.

Block 12 of FIG. 5 shows the ultrasonics equipment of the installation of the invention, containing electronic devices to transmit ultrasonic pulses with variable frequency and variation, independent programmable gain amplifiers for each transducer, means to apply attenuation-distance corrections and means to detect the envelope of the amplified signals.

Block 13 of FIG. 5 shows the local processor used in the installation of the invention, which controls the ultrasonics equipment 12, determining when each channel should be activated according to the signals provided by the wheel presence detectors 11 and receiving (digitally) the ultrasonic plots from the ultrasonics equipment 12. The local processor 13 may make calculations to analyze the signals and apply the evaluation algorithms for the condition of the rolling band and surface of the wheels 9.

Block 14 of FIG. 5 shows the computer used in the installation of the invention, which is the means by which the operator is related to the system. It is connected to the local processor 13 of the system (up to a distance of 1200 m) and is responsible to give activation orders of the ultrasonics equipment 12 and to collect, organize and store the measurement results, as well as to generate the relevant pulses. The computer 14 is connected to an antenna 15, permitting the identification of the measured train compositions. The computer 14 may be connected and simultaneously control measurement equipment of other parameters.

Figure 6:
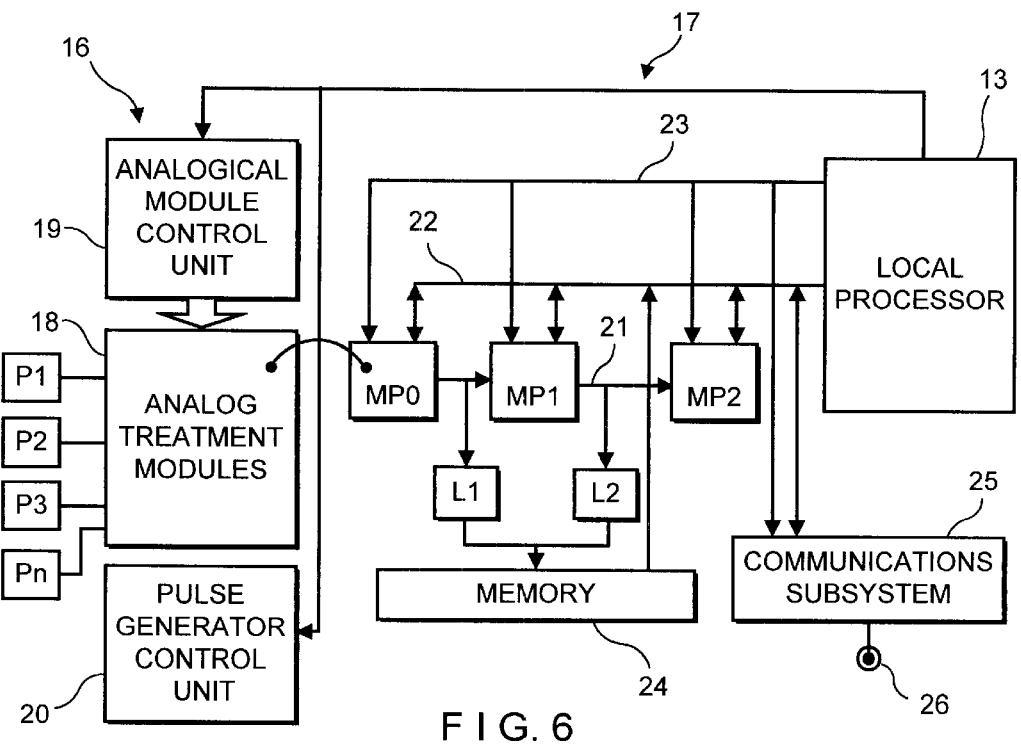
FIG. 6 is a general structural diagram of the ultrasonics equipment and local processor used in the installation of the invention.

The general structure of the ultrasonics equipment 12 and the local processor 13 of the installation of the invention is shown in FIG. 6 of the drawings, in which it can be seen that there is an analogical part 16 and a digital part 17. The analogical part consists of analogical treatment modules 18 of the ultrasonic signals to be captured and includes programmable gain amplifiers (80 dB, 20 MHz) and prefiltering, detection, logarithmic amplification (100 dB) and channel multiplexing stages. Moreover, there is an analogical module control unit 19 and a pulse generator control unit 20, which will be described later.

The digital part 17 consists of a powerful digital processing system, permitting the application in real time of complex algorithms to the ultrasonics signals captured. The core of said digital part 17 is a bus 21 with segmented architecture and a set of high efficiency dedicated processor modules MP0, MP1, MP2 . . . joined to an 8 bit data line 22 and a 8 bit address line 23. The bus 21 consists of segments separated by baseboards over which the processor modules MP0, MP1, MP2, . . . are housed. The outputs of said processor modules are joined to buffer memories L1, L2 capable of temporarily storing the incoming information flow and providing data as required for processing, the output of said buffer memories being joined to an intermediate result capture memory 24.

The diagram in FIG. 6 is completed with the local processor 13, the communications control unit 25 and the series output 26.

The capture and processing of each signal with the system shown in FIG. 6 may be developed in three stages:

Stage 1: Programming of Parameters

During this stage, all the values required for an acquisition that should be modified with respect to the previous acquisition are established, as well as the digital processing parameters. The configuration modifications of the modules are also made in this stage.

Parameter programming is made by means of readings and writing in the system control bus addresses. The operation is asynchronous and its duration closely depends on the number of reading-writing cycles required to fix all the parameters. In the system of FIG. 6, this operation depends on the local processor 13.

Stage 2: Acquisition and Processing

This starts with the generation of a triggering of the transducer of a feeler P, the digitalizing of the received signals and their digital processing in the system chain of FIG. 6 and terminates when the last information sample requested is available in the results memory 24.

In the system of FIG. 6, these two operations are concurrently performed following a consumer-producer mechanism. Nevertheless, the digitalizer module of the digital processing part 17 always captures a certain number of samples prior to the event determining acquisition and processing. In this state, the later processing chain is maintained waiting the programme trigger event (crossing of threshold, determination of the delayed time, triggering by software, external triggering, etc.). The end of the acquisition is determined with the programming of the number of samples to be digitalized. The sequence of samples contained in an acquisition is called plot.

Processing is made following a forced transfer mode at a constant speed of 10 Msamples/s. Hence, a window frame is opened every 100 ns, during which the modules having any result deliver it to its successor in the chain. This operation mode has been selected to present a very simple control, where the timing involved are not critical. A master clock of 20 MHz maintains the synchronism throughout the entire chain.

It is important to indicate that several circumstances exists by which an acquisition and processing sequence may be implemented but not terminated. These situations have their origin in different causes: the non-appearance of a triggering event, abnormal operation of the circuitry, activation of protections, etc. The application software should recover from these exceptional situations automatically and if possible, transmit a diagnosis of their causes.

Stage 3: Results Transfer

Generally, the results are collected over a memory from the output of any of the configured modules MP0, MP1, MP . . . ). The circuits incorporated in the base card facilitate the selection of any module as a results source, being of great assistance in research and evaluation jobs (for example, real time comparison of signals before and after a determined processing).

Nevertheless, on other occasions, the modules themselves store the results obtained, being read through the control bus. This option permits the availability of several simultaneous pieces of information referring to the same acquisition, being specially useful in the case of peak detection.

The maximum parallelism in the operation of the processor modules MP0, MP1, MP2, . . . is maintained although some of them require more clock cycles to complete their calculations. For this reason, as already has been said, these modules have buffer memories L1, L2 capable of temporarily storing the incoming information flow and providing data as required for processing.

Figure 7:
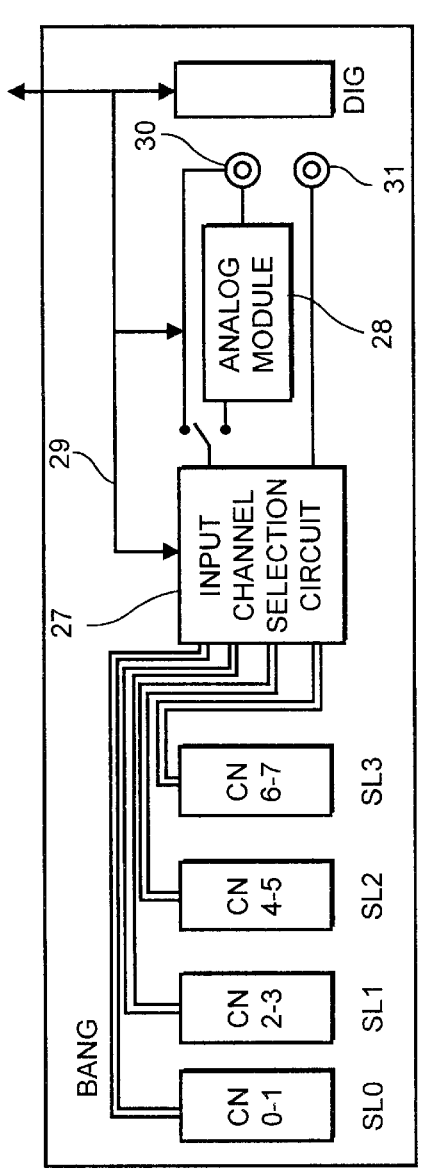
FIG. 7 is a view of the analogical base card used by the invention.
Figure 8:
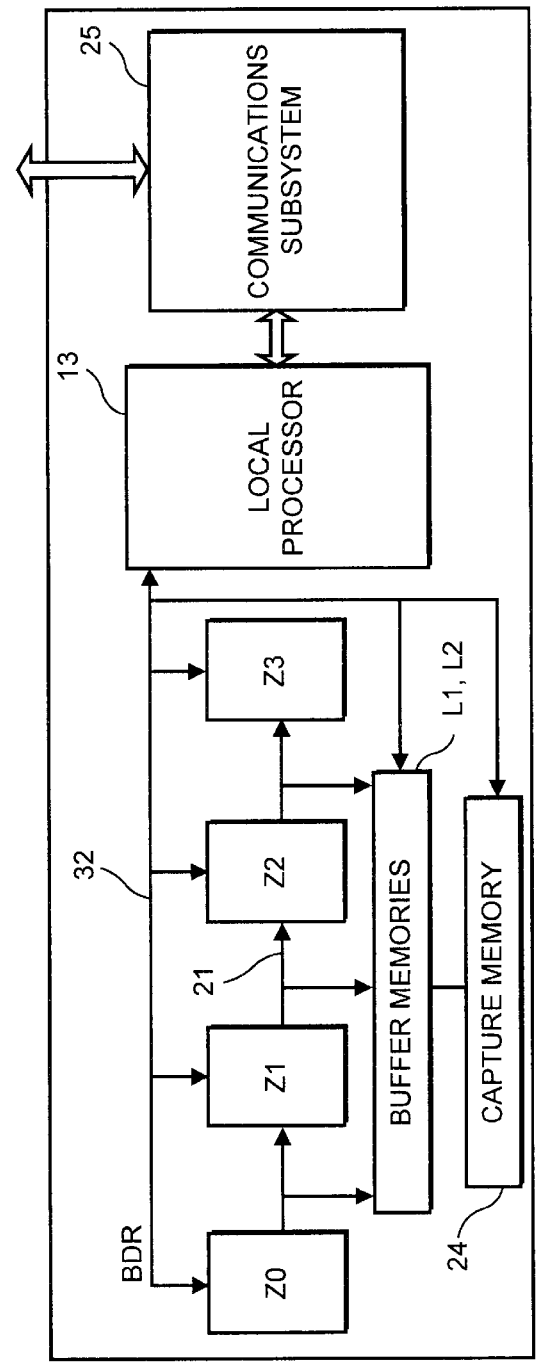
FIG. 8 is a view of the remote digital base card used by the invention.

The physical structure of the system represented in FIG. 6 consists of two base cards on which the digital and analogical processing modules are housed: the analogical base card BANG (FIG. 7) and the remote digital base card BDR (FIG. 8). The power supply 33 (see FIG. 9) is added to these two components.

The analogical base card BANG serves as a support for the analogical amplification-filtering modules across the four slots SL0, SL1, SL2, SL3, each one including two analogical channels CN. Hence, the slot SL0 includes the CN0–1 channels, the slot SL1, the CN2–3 channels, the slot SL2, the CN4–5 channels and the slot SL3, the CN6–7 channels. Moreover, the BANG card contains a stabilized voltage production system to supply the analogical modules, the input channel selection circuitry 27 and an analogical module 28 for envelope detection. These modules are governed across the control bus 29.

The card BANG includes an additional slot DIG directly joined to the control bus 29 and permits the addition of a digital input-output card (in this case, for the detection of wheels 9).

The card BANG is completed with a signal output 30 and a gain control unit 31.

The remote digital base card BDR serves as a support for the digital and hybrid architecture processing modules, which are inserted in four baseboards Z0, Z1, Z2, Z3 joined to the control bus 32. Each baseboard is joined to the following one by means of the segmented signal bus 21 through which it receives the processed data by the previous module and delivers its results to the following module. The output of each module may also be directed to the results memory 24, passing through the buffer memories L1, L2 of the temporary storage.

The card BDR contains, moreover, the communications control unit 25 for the reception of orders and transmission of results and the entire system is governed by the local processor 13, entrusted with programming the modules, attending the communications and triggering signal acquisition.

Figure 9:
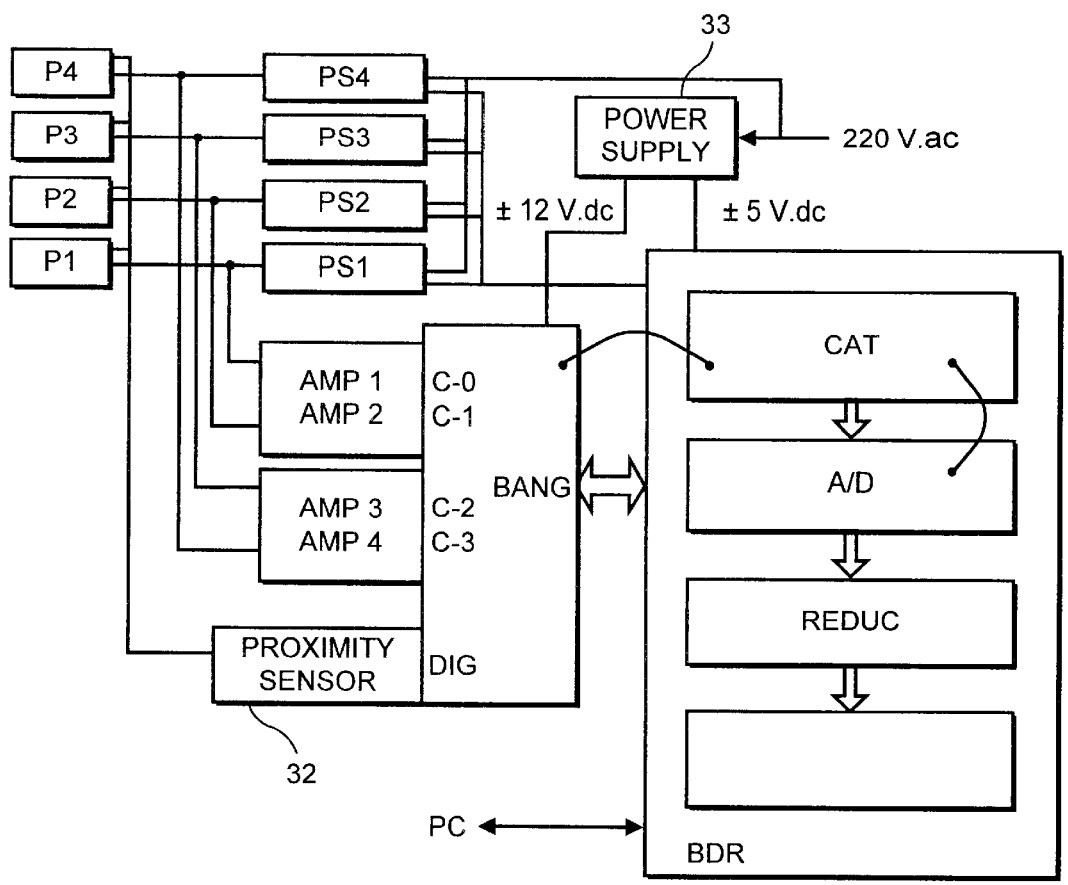
FIG. 9 is a block diagram of the ultrasonics equipment of the installation of the invention, applied to the detection of cracks in railway vehicle wheels.

In FIG. 9, the ultrasonics equipment 12 configuration is shown as used for the detection of cracks in the installation of the invention. It consists of four programmable pulse generators PS1, PS2, PS3, PS4 connected to the feelers P1, P2, P3, P4 and to two amplification modules, each one of which incorporate two linear amplifiers AMP1, AMP2, AMP3, AMP4 with programmable gain, installed in the CN0–3 channels of the analogical base card BANG. A control module 32 of the proximity sensors 11 is installed in the digital input-output slot DIG of the card BANG, a gain control module CAT is installed in the baseboard Z0 of the remote digital base card BR, an analogical/digital conversion module A/D is installed on baseboard Z1 of the card BDR and a data reduction module (REDUC) is installed on baseboard Z2 of the card BDR. The local processor 13 installed on the card BDR executes the programme to manage the specific modules dedicated to the detection of cracks in railway vehicle wheels 9.

A power supply 33 receives a voltage of 220 V in alternating current and supplies a voltage of +/−12 V in direct current to the card BANG and a voltage of +/−5 V in direct current to the card BDR.

Operation of the Installation of the Invention

When the measurement order is received from the computer 14, the installation operates as follows:

1. The local processor 13 programs components of the ultrasonic equipment 12 according to the supplied parameters (frequency and duration of the pulses emitted, amplifier gain, digitalization frequencies, etc.). Actions still not developed may also be included here, like moving the feelers P to the measurement position in the rail beam 1.

2. The local processor 13 interrogates the wheel detectors 11 of each feeler P and when any one informs of the presence of a wheel 9, it orders the ultrasonics equipment 12 to transmit the programmed pulse and collect and condition the signals detected by this feeler. These signals correspond both to the propagation of the pulse transmitted in successive revolutions of the wheel 9 and to the echoes produced by the imperfections present on the surface of the rolling band of each wheel. This digitalized signal is stored in the local processor 13 for later analysis.

3. When the computer 14 gives the signal to stop measuring, the local processor 13 analyzes the stored signals and gives an evaluation of the state of each measured wheel 9 and this evaluation is transmitted to the computer 14.

Algorithm for the Evaluation of Ultrasonic Plots of Train Wheels.

In the following lines, the detection system of cracks in the rolling band of train wheels is described, using the installation of the invention explained above with reference to the drawings. Two 1 MHz surface waves ultrasonic feelers P1, P2; P3, P4 are used on each railway line, an ultrasonics equipment 12 to generate the ultrasonic plots when the wheels 9 pass over each feeler and a computer 14 to collect the plots, assign them to the corresponding wheel and evaluate them. The computer 14 is connected to an antenna 15 which reads the identifiers for the measured train compositions. With this arrangement, two plots per each wheel are obtained, offset 120° approximately.

The ultrasonics equipment 12 is as shown in FIG. 9 and consists of the same number of programmable pulse generators and modules appearing in said drawing.

The parameters fixed for the generation of wheel 9 plots are as follows:

Ten 1 MHz excitation pulses at a given amplitude.
Amplifier gain at 50 dB.
Sampling frequency, 8 Msamples/s.
Length of the presample plots 20 and 16,980 samples.
Reduction factor 32.

Characteristics of the Ultrasonic Plots

Figure 10:
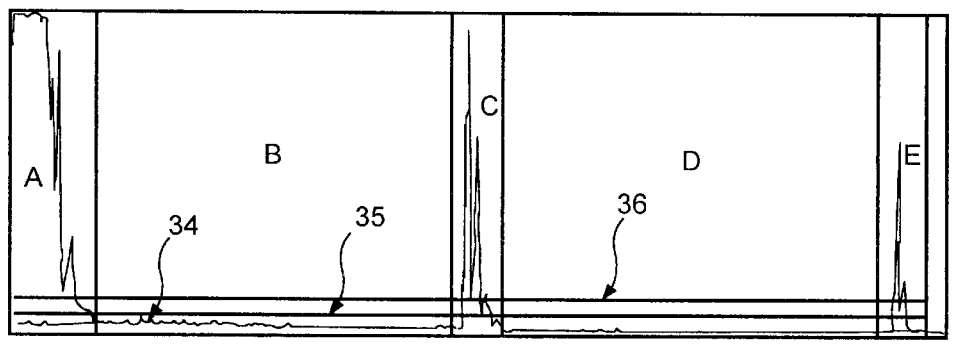
FIG. 10 shows ultrasonic plot of a wheel obtained with the installation of the invention.

In each plot the five zones appearing in FIG. 10 of the drawings may be distinguished.

A. Feeler excitation pulse.
B. Inspection zone of the first half of the wheel.
C. First direct transmission pulse (half wheel).
D. Inspection zone of the second half of the wheel.
E. Second direct transmission pulse (end of wheel).

While the extension of zone A is determined by the system, the position and size of the remaining zones depend on the wheel 9 dimensions, the type of steel it uses and the temperature.

The imperfections in the state of the wheel 9 rim are shown by echoes appearing in the zones B and D, the good operation of the pulse generator PS and the feeler P is indicated by the presence of a pulse from zone A, whilst the echoes in zones C and E reveal the coupling quality between feeler P and wheel 9.

Plot Parametrization

The first step to evaluate the wheel 9 condition consists in detecting and parametrizing the echoes appearing on the plot. The process is carried out as follows: determination of the base line 34 of the plot, establishing the detection thresholds 35 and echo validation, echo identification and parametrization, direct transmission echo identification and correlation between echoes.

Obtaining the Base Line and Establishing the Detection Threshold and Echo Validation The base line 34 of the plot marks the ultrasonic signal level in the zones free from defects of the wheel 9. To approach this level, do the following:

1. The mean value and the standard deviation of the plot points, excluding zone A, are calculated.

2. A new plot is produced with the points of the original plot whose amplitude is less than the mean plus the standard deviation calculated in step 1.

3. The mean value and standard deviation of the plot points generated in step 2 are calculated. This mean value is used as an amplitude estimate of the base line 34, while the standard deviation marks the level of the intrinsic noise of the inspected wheel 9.

4. The detection threshold 35 marks the amplitude above which it is considered that the signal can belong to an echo, which to be validated as such, should exceed at any moment the validation level 36. In the present case, the base line 34 itself has been used as a detection threshold 35 and as validation level 36, the value of the base line 34 plus four times the standard deviation calculated in step 3. Moreover, these values are used to determine the validity of the plot (wheel presence detection). The plot is considered valid if the mean plus the standard deviation exceeds the value 0.001.

Echo Detection and Characterization

To locate the echoes in the plot, follow the steps below:

1. The plot points are followed in order until finding one exceeding the detection level and taking this point as the start of an echo.

2. The plot points are followed until its value is less than the detection level again, marking this point as the end of the echo. If any of the echo points exceeds the validation level 36, the echo is added to the list of detected echoes.

3. Steps 1 and 2 are repeated until finishing the plot.

4. The echo list detected is corrected by merging in a single echo those whose termination was less than three points from the following echo.

5. For each echo, the following is noted: the starting point, its width in points, the position and amplitude of the maximum value of the echo and the sum of the amplitudes of all the points comprising it.

Identification of Direct Transmission Echoes

The following step consists in determining the position and relative distance of the direct transmission echoes (location of zones C and E of the plot). The way to do this depends on the number of valid plots of the wheel 9 available:

1. If there are two plots, an hybrid plot is generated as the point to point minimum of each one of them and in this way, all the echoes not appearing in the same position are eliminated (the direct transmission echoes coincide in the two plots of the same wheel). For this plot, a list of echoes of the form described in the two previous sections is generated.

2. The echo list of the hybrid plot is followed if two plots are available or if only one of the valid plots is available and pairs of echoes are searched in which the starting point of one of them is double the distance from the starting point of the other, with a tolerance factor of 15 points and which starts at more than 150 points from the origin. If several points of pulses exist which satisfy this condition, the pair most distant from the plot origin is selected.

3. If the calculated transmission echoes come from an hybrid plot, their identification is started using the echo list of each one of the original plots. For the latter, those echoes having a non-void intersection with the transmission echoes of the hybrid plot are searched for in each one of the lists. If any of the echoes identified had a width greater than 35 points, an echo with a width equal to the echo corresponding to the other plot is separated from it, and the rest is added to the list as independent echoes.

Correlation Between Echoes

Then, the echoes of the list appearing in zone D of the plot and which are a replica of an echo of zone B are identified for each plot:

1. The distance between replicas is determined as the distance between the direct transmission echoes obtained.

2. For each echo of zone B of each plot, it is checked if any one exists in zone D having its starting point at the distance between calculated replicas, with a tolerance factor of 10 points. If this condition is satisfied, the echoes are marked as "replica possessor" and "replica", respectively.

If two valid plots of the wheel 9 are available, the echoes of the two plots which had been originated by the same reflector are identified. For the latter, it should be taken into account that the distance between the two feelers P1, P2; P3, P4 of the same railway line 8 is approximately 870 mm, which, taking 3000 m/s as the value of the speed of sound in steel and with the acquisition parameters used, it makes the signals of the feelers P2 and P3 more advanced by 140 points with respect to that of the feelers Pi and P4 respectively. The process is as follows:

1. For each plot, its length equal to the starting value of the second direct transmission echo is fixed.

2. For each peak of each plot not marked as a replica, a peak is searched for in the other plot starting or terminating 140 points before (if the examined echo belongs to a feeler P1 or P4 plot) or 140 points afterwards (if the echo comes from the feelers P2 or P3), than the echo analyzed, with a tolerance factor of 6 points. If any peak is found, both are marked as corresponding echoes. If the possible echo falls in zones A, B or E, the echo is marked as a corresponding to a dead zone. (The advance or delay calculations are made taking as a module the length calculated for the plot).

Wheel Evaluation

In this first phase, the evaluation of the wheel 9 condition is made by attending only to the value of the maximum of each detected echo and to its width and is based on the hypothesis that the echoes produced by cracks should be of a large amplitude and on the observation that very wide echoes usually correspond to drifters and plans.

The evaluation algorithm is developed as follows:

1. If none of the plots obtained for wheel 9 is marked as a valid plot, the wheel is marked as non-appraisable.

2. If the direct transmission echoes have not been detected, the wheel 9 is marked as non-appraisable.

3. If the conditions fixed in 1 and 2 do not occur, each peak of each plot marked as valid is evaluated separately. The value of an echo is determined by means of the linear function of the maximum value, which assigns the zero value to echoes with a maximum value equal to zero and 2.5 to echoes with an amplitude 255. The assigned value is increased by 0.5 if the maximum of the echo is greater than 250.

4. The optimum width of the echo is determined by means of a linear function assigning an optimum width of zero to echoes with a maximum of zero and of 20 points to echoes with an amplitude maximum of 255. If the real width is greater than the optimum width calculated, the echo is penalized by assigning it 85% of the value assigned in step 3.

5. The maximum of the peak values assigned in steps 3 and 4 is determined from among all the echoes of all the valid plots, rounding off to the nearest whole number (or to 1 if the result is 0) and this value is fixed as the wheel value.

Proceeding in the way indicated by the invention, it is possible to detect at an early stage the cracks which will possibly exist in the rolling band of a wheel, whilst the train is moving and adopts the corresponding repair measures before the cracks increase in size and cause greater damage to the wheel, such that safety of railway traffic is considerably increased.

Although in the previous description, the essential characteristics of the invention has been stressed, it is understood that the latter can be modified in form and detail, respecting the scope of the invention. For example, the number of feelers, pulse generators, modules and other components may be different from that illustrated. Therefore, it is intended that the scope of the invention is solely and exclusively limited by the contents of the attached claims.

What is claimed is:

1. An installation for the automatic evaluation of the condition of the rolling band on wheels of moving trains, especially for the detection of cracks in said rolling band, which comprises a support structure made of steel, consisting of a rail beam (1) for each railway line (8), replacing a section of the line and over which the flange of the train wheels (9) is made to run, assuring continuity between the rail beam and the railway line by means of a bolted joint (3); a guard-rail (2) attached to said rail beam to ensure guidance of the wheels while they move, bearing with their flange against the rail beam; feelers (P) adapted to come into contact with the wheels passing over them; feeler holders (4) installed on the rail beam and each provided with two guides (5) and a swinging spring (6), such that the passage of the wheels over the feelers forces and assures contact between the wheels and the feelers; ultrasonic equipment (12) to transmit to the passing wheels, ultrasonic pulses with programmable frequency and duration and to generate and acquire ultrasonic plots corresponding to the wheels; a local processor (13) to control the ultrasonic equipment and receive from it, generated digital signals from the ultrasonic plots; a computer (14) connected to the local processor for transmitting activation orders of the ultrasonic, equipment, collecting, organizing and storing measurement results and generating pertinent reports; and an antenna (15) connected to the computer to identify measured train compositions, said ultrasonic equipment (12) being designed for generation, acquisition, and processing in real time, said ultrasonic signals for the execution of non-destructive testing of materials and comprising an analog part (16) and a digital part (17), said analog part comprising analog treatment modules (18) for treating the ultrasonic signals to be acquired, including programmable gain amplifiers for prefiltering, detection, logarithmic amplification, and channel, multiplexing stages, said digital part including a bus (21) with segmented architecture and a set of dedicated processor modules (MP0, MP1, MP2, . . . ) said bus consisting of segments separated by board bases over which the processor modules are housed, said analog part (16) being housed on an analog base card (BANG) serving as a support for the analog modules through a series of slots (SL0, SL1, SL2, SL3, . . . ) with respective analog channels (CN0–1, CN23, CN4–5, CN6–7, . . . ) and further comprising a stabilized voltage generation system for supply to the analog modules, input channel selection circuitry (27) and an analog module (28) for envelope detection, said modules being governed through a control bus (29) of the analog base card.

2. An installation according to claim 1, wherein the feeler holders (4) may be activated and deactivated to move vertically by means of two respective guides (7).

3. An installation according to claims 1, which includes at least two said feelers (P1, P2; P3, P4) for each railway line (8).

4. An installation according to claim 3, which includes four of said feelers for each rail.

5. An installation according to claim 1, wherein each one of the feelers (P) consists of a piezoelectric transducer to generate and receive ultrasonic surface waves, using a dry coupling means and incorporating two inductive proximity detectors (11) to indicate the presence of a wheel (9) over the transducer.

6. An installation according to claim 5, wherein the surface waves generated and received by each transducer are of 1 MHz and the dry coupling means used in each transducer is a crude rubber film.

7. An installation according to claim 1, wherein said programmable gain is 80 dB at 20 MHz and said logarithmic amplification is 100 dB.

8. An installation according to claim 1, wherein said analog part includes an additional slot (DIG) joined directly to the control bus (29) to add a digital input-output card for the detection of said wheels (9).

9. An installation according to claim 8, wherein the digital part (17) of the ultrasonic equipment (12) is housed on a remote digital base card (BDR), which serves as a support for the digital and hybrid architecture processing modules, which are inserted on baseboards (Z0, Z1, Z2, Z3, . . . ) joined to the control bus (32) of the digital base card, each baseboard being joined to the following baseboard by means of the segmented signal bus (21) through which it receives the data processed by the previous module and delivers its results to the following module, and the output of each module being joined to a results memory (24), said digital base card further containing a communications subsystem (25) for the reception of orders and transmission of results, said local processor (13) governing the entire digital base card and programming the modules, attending the communications and triggering the acquisition and processing of signals.

10. An installation according to claim 9, wherein both the analog base card (BANG) and the remote digital base card (BDR) are connected to a power supply (33).

11. An installation according to claim 9, wherein the analog base card(BANG) incorporates four said slots (SL0, SL1, SL2, SL3) with two said analog channels (CN0–1, CN2–3, CN4–5, CN6–7) for each of said slots and the remote digital base card (BDR) having four baseboards (Z0, Z1, Z2, Z3).

12. An installation according to claim 1, wherein the ultrasonic equipment (12) further includes a series of programmable pulse generators (PS1, PS2, PS3, PS4, . . . ) connected to the feelers (P1, P2; P3, P4, . . . ) and to the amplification modules, a proximity sensor control module (32) installed in a digital input/output slot (DIG) of the analog base card (BANG) and a gain control module (CAT), an analog/digital conversion module (A/D) and a data reduction module (REDUC) being installed on the remote digital base card (BDR).

13. An installation according to claim 12, wherein four of said programmable pulse generators (PS1, PS2,PS3, PS4) are provided and two amplification modules, are installed on the analog base card (BANG-), each of which includes two linear amplifiers (AMP1, AMP2, AMP3, AMP4) with variable gain.

* * * * *